United States Patent [19]

Hawke et al.

[11] Patent Number: 5,747,347
[45] Date of Patent: May 5, 1998

[54] LABELLED CARBOHYDRATES AND THEIR USE IN ASSAYS

[75] Inventors: David Harry Hawke, Newportville, Pa.; Rajesh Bhikhu Parekh, Oxford, United Kingdom; Paul Goulding; Stephen Alexander Charles, both of Oxon, United Kingdom

[73] Assignee: Oxford Glycosystems Ltd., Abingdon, Oxon, United Kingdom

[21] Appl. No.: 545,790

[22] PCT Filed: May 20, 1994

[86] PCT No.: PCT/GB94/01116

§ 371 Date: Mar. 19, 1996

§ 102(e) Date: Mar. 19, 1996

[87] PCT Pub. No.: WO94/28423

PCT Pub. Date: Dec. 8, 1994

[30] Foreign Application Priority Data

May 20, 1993 [GB] United Kingdom ............ 9310467

[51] Int. Cl.$^6$ ............ G01N 33/00; C07H 1/00; C08B 35/00
[52] U.S. Cl. ............ 436/94; 436/56; 436/95; 436/161; 436/172; 536/1.11; 536/17.2; 536/104; 536/123.1; 536/123.13
[58] Field of Search ............ 436/56, 94, 95, 436/161, 172; 536/1.11, 17.2, 104, 123.1, 123.12

[56] References Cited

U.S. PATENT DOCUMENTS 4,322,409 3/1982 Yoshikumi et al. ............ 424/180

FOREIGN PATENT DOCUMENTS

WO 86/06374 11/1986 WIPO.
WO 91/05256 4/1991 WIPO.

OTHER PUBLICATIONS

J. C. Irvine et al, *J. Chem. Soc.* 1909, 95, 1545–1555.
H. Bisswanger et al, *Biochemistry* 1979, 18, 5946–5943.
M. Yalpani et al, *Can. J. Chem* 1981, 59, 2934–2939.
J.W. Webb et al, *Anal. Biochem.*, 1988, 169, 337–349.
P.P. Sanders et al, *Anal. Biochem*, 1962, 3, 354–356.
E.R. Ocaranza et al. *Chem. Abstr*, 1965, 62, 806d.
H.H. Baer et al. *J. Org. Chem.*, 1969, 34, 3848–3853.
W.T. Wang et al., *Anal. Biochem.*, 1984, 14, 366–381.
A.P. Winiski et al., *Biochemistry*, 1988, 27, 386–392.
L. Poulter et al., *Anal. Biochem.*, 1991, 195, 1–13.
K.R. Anumula et al., *Peptides* 1992, 13, 663–669.
C.J. Edge et al., *Proc. Natl. Acad. Sci USA* 1992, 89, 6338–6342.
S. Sonoki et al., *J. Liq. Chromatog.* 1993, 16, 343–352.
D. Ghosh et al., *chromatographia* 1993, 37, 543–545.
K.R. Anumula *Glycobiology* 1993, 3, 511.
K.R. Aumula *Anal. Biochem.* 1994, 220, 275–283.
D.H. Hawke et al., "Techniques in Protein Chemisry III" R.H. Angeletti ed. Academic Press, Inc: New York, 1992, 315–326.
J. Biochem. vol. 85, No. 4 (1979), "Analyses of Oligosaccharides by Tagging the Reducing End with a Fluorescent Compound", pp. 989–994, Sumihiro Hase et al.
Canadian Journal Of Chemistry, vol. 59 (1981), Ottowa, CA., "Synthesis of fluorescent probe–carbohydrate conjugates", M. Yalpnai et al., pp. 2934–2939.
Journal Of Heterocyclic Chemistry, vol. 7 (1970), Provo, us., "Synthesis of 10–deazariboflavin and related 2, 4–dioxopyrimido [4,5–b]quinolones", D.E. O'Brian et al., pp. 99–105.
Biochemistry, vol. 18, No. 26 (1979), Easton, PA., "N–(5–Phosphoribosyl)anthranilate Isomerase–Indoleglycerol–phosphate Synthase. 1. A Substrate Analogue Binds two Different Binding Sites on the Bifunctional Enzyme from *Escherichia coli*" Hans Bissanger et al., pp. 5946–5953.
Chemical Abstracts, vol. 75, No. 17 (1971), Ohio, US., "Potential Cytostatics. 25. Salts and amides from (4–[bis(2–chloroethyl)amino]benzoic acid and 1–methylamino–1–deoxy sugar alcohols", H. Dorn et al., pp. 455–456.

*Primary Examiner*—Arlen Soderquist
*Attorney, Agent, or Firm*—Oliff & Berridge, PLC

[57] ABSTRACT

A method for distinguishing between carbohydrates or glycoconjugates in a mixture thereof, wherein the or each carbohydrate or glycoconjugate is a hydrophilic fluorescently-labelled saccharide molecule, wherein the label is a —NR—Ph—CO— group, wherein R is selected from H and substituents, and Ph is phenylene.

14 Claims, No Drawings

LABELLED CARBOHYDRATES AND THEIR USE IN ASSAYS

FIELD OF THE INVENTION

This invention relates to carbohydrates and in particular to (oligo)saccharides conjugated with a label which facilitates their identification and analysis.

BACKGROUND OF THE INVENTION

Oligosaccharide analysis may be performed by a variety of standard techniques including, but not limited to, gel filtration, ion exchange, hydrophobic interaction and hydrophilic interaction chromatography, mass spectrometry, gel electrophoresis and capillary electrophoresis. Tritium-labelling is often used. There are also several reports detailing methods, especially by reductive amination, for labelling the reducing terminus of an oligosaccharide with, for example, UV-absorbing, fluorescent, or electro-chemically active labels.

Many laboratories would prefer to avoid the use of radio-isotopes. For example, WO-A-9105256 discloses labelling carbohydrates with a fluorescent naphthalene ring structure which includes a charge-carrying substituent, for the purpose of separating and analysing the carbohydrates. The preferred labelling reagents are aminonaphthalenesulphonic acids.

Such labels for oligosaccharides are generally relatively large, charged molecules, making them unsuitable, for instance, for the gel filtration chromatography of uncharged (oligo) saccharides,e.g. using Bio-Rad P4 gels.

Smaller labels, e.g. p-aminobenzoates, have been used in mass spectrometry. However, they are liable to undergo hydrolysis at elevated pH.

Relatively small fluorescent labels are also known. For example, Hase et al, J. Biochem. 85:989–994 (1979), disclose 2-aminopyridine for use as a fluorescent label for oligosaccharides and their separation by paper electrophoresis. Yalpani et al, Can. J. Chem. 59:2934–2939 (1981), disclose bicyclic, e.g. naphthalenic, labels and also p-fluoroaniline as a starting material for fluorescent labelling, via p-fluorochlororoacetamidoaniline (i.e. Cl—CH$_2$—CO—NH—Ph—F wherein Ph is 1,4-phenylene), of 1,2:3,4-di-O-isopropylidene-α-D-galactopyranose.

Bisswanger et al, Biochemistry 18(26):5946–5953 (1979), report investigation of tryptophan biosynthesis, specifically of the multifunctional enzyme (phosphoribosyl) anthranilate isomerase-indoleglycerol phosphate synthase. N-(5-phosphoribosyl)anthranilate was prepared and identified as a substrate of greater stability and purity than the natural substrates. This synthetic substrate was reported as having different absorption and fluorescence spectra on binding to each of the enzyme's two binding sites.

O'Brien et al, J. Het. Chem. 7:99–105 (1970), disclose the synthesis of antiriboflavin compounds using as starting materials dimethylanthranilic acid and anthranilic acid. However, the anthranilic compounds were used here only as synthesic precursors and not as fluorescent labels.

SUMMARY OF THE INVENTION

According to the present invention, a saccharide is labelled with a fluorescent group of the formula —NR—Ph—CO—, e.g. —NR—Ph—COO— or —NR—Ph—CONR'—.

The labelled compounds are stable, soluble in water and also organic solvents such as DMSO. For example when the group is —NR—Ph—CONR'—, they are uncharged but run satisfactorily on gels. R and R' may independently be H, C$_{1-6}$ alkyl, e.g. methyl, or any substituent provided that the fluorescent property, and adequate hydrophilicity, are retained. Ph is phenylene.

DESCRIPTION OF THE INVENTION

The label may be attached by reaction with reducing sugars under a variety of conditions, in the presence of a reducing agent (may be added sequentially) such as sodium cyanoborohydride, or a borane-amine complex, such as the borane-dimethylamine complex. After reaction, the derivatised saccharide may be purified by various methods, or directly analysed on, for instance, P4 gel filtration chromatography.

The novel compounds may be readily prepared from readily-available starting materials, by reductive amination of the reducing terminal of a saccharide. For example, the saccharide (represented as oligo—CHO) may be reacted with an anthranilamide, e.g. 2-aminobenzamide, as shown in Chart A. Either or each N atom may be substituted by R/R' as defined above; the groups R' may be the same or different. The benzene ring may also be substituted by such groups. A m- or p-aminobenzamide may also be used.

Alternatively, the saccharide may be derivatised and then reacted with an isatoic anhydride, as shown in Chart B (in which case Ph is o-phenylene). In either case, either or both reagents may be in the form of a reactive derivative. For example, a saccharide may be treated in known manner to form a hydrazone whose terminal group may be protected, e.g. by acetylation; the hydrazone may then be reduced to a hydrazine, for example with a known reducing agent such as borane-dimethylamine complex or sodium cyanoborohydride, to give the partial formula —N*H—NHAc; the product is then reacted with isatoic anhydride (or analogue thereof). In the given partial formula, the asterisk indicates the N atom that is attached to the carbohydrate, and is susceptible to electrophilic reagents.

In the Charts, the fluorescent group is —NR—Ph—CONR'—. Alternative groups include —NR—Ph—COO—, as derived from anthranilic acid. Specific, illustrative fluorescent groups are —NH—(o—Ph)—CONH$_2$ and —NH—(o—Ph)—COOH.

Compounds of the invention are glycoconjugates, because the label is present. The saccharide, i.e. a monosaccharide or oligosaccharide, may be a carbohydrate which has been derived from a glycoconjugate, e.g. a glycolipid, glycohormone, or glycopeptide. It is preferably labelled at or, via any suitable linker, to the reducing terminus of the terminal (or one, if a monosaccharide) saccharide moiety.

Labelled saccharides of the invention are very suitable for use in a wide range of separation systems, for assay purposes. In particular, CZE or gel electrophoresis may be used.

It has been found that 2-aminobenzamide (2AB) provides substantially stoichiometric labelling of a pool of sugars, without selectivity, while the known label 2-aminopyridine has not been shown to be stoichiometric. As a label, 2AB is thus equivalent in efficiency and selectivity to tritium. It is simple to use, and causes minimal degradation, e.g. no or substantially no desialylation, of sugars. Further, 2AB-labelled glycans may be analysed by most conventional chromatographic, mass-spectrometric and spectroscopic techniques. The 2AB label is stable even under extremes of acidic and alkaline conditions and does not interfere with the action of exoglycosidases. If 2AB-labelled glycans are analysed chromatographically, it should be noted that their chromatographic behaviour will generally be different from that of underivatised glycans.

The following Examples illustrate the invention. Example 1 is in the nature of a protocol. Examples 2 and 3 specifically utilise 2-aminobenzamide (2AB) and anthranilic acid (2AA) as labels.

EXAMPLE 1

Materials

Vial A: Dye, e.g. 2AB
Vial B: DMSO (350 µl) GlycoPure
Vial C: Acetic Acid (200 µl) GlycoPure
Vial D: Reductant, e.g. sodium cyanoborohydride Sample Preparation:

The glycan sample to be labelled, whether a purified glycan or a glycan mixture, should contain a free reducing terminus and be salt-free. Glycans can be readily de-salted using either cation and/or anion exchanges (provided that the latter do not adsorb any acidic glycans) or by gel-filtration. An amount (in the range 10 picomoles–50 nanomoles) of the de-salted glycan(s) to be labelled should be transferred to a clean, 0.5 ml Eppendorf just prior to commencing labelling. Care should be taken when handling unreduced glycans to avoid contamination with environmental carbohydrate.

Procedure:

1. Transfer salt-free glycans to a clean Eppendorf tube, and evaporate (rotary vacuum evaporator) to dryness (at a temperature of <27° C., if glycans are sialylated).
2. Add 150 µl Vial C to Vial B and mix. Add 200 µl of this mixture to Vial A and mix until dye is dissolved. Add 100 µl of dye solution in Vial A to Vial D and mix until reductant is dissolved (may require vortexing). This last addition should be performed in a fume hood.
3. Add 5 µl of final labelling reagent in Vial D to each dried glycan sample, cap the Eppendorf tube, mix thoroughly, and incubate at 65° C. for 120±15 minutes.
4. At the end of incubation, spot (using a standard pipetter) with a single transfer the entire reaction mixture to the marked region of a paper strip. The strip may be marked with a pencil at the tip furthest from the origin for sample identification. Allow the spot to dry at room temperature, transfer the strip to a rack and place the rack in a pre-equilibrated chromatography tank.
5. When the solvent front is within 10 mm of the end of the paper, gently remove the rack and stand upright in a fume-cupboard to dry (20 to 30 minutes). Discard solvent from the tank.
6. Cut the strip to a width of 5 mm on each side of the origin and roll the cut portion of paper (as necessary) containing the origin, transfer it to a luer-locked syringe, fitted with filter, inserted into a clean tube (glass or plastic). Add 1.0 ml of water directly onto the paper, ensuring that it is thoroughly wetted and submerged. Leave for 5 minutes then centrifuge (3500 rpm) for 10 minutes.
7. Remove the tube containing labelled glycans, evaporate to dryness, resuspend in a desired volume of water or solvent for further analysis.
8. (Desialylation) Transfer an aliquot of each of the glycan pool in 35 µl water to a 0.7 ml Eppendorf vial.

Add 10 µl of sialidase solution in 500 mM sodium acetate buffer, 0.1 unit per digest, to each glycan pool. Incubate the capped vial at 37° C. for 14 to 16 hours. At the end of the incubation, proceed to preparation of labelled glycans for fractionation using the RAAM 2000 GlycoSequencer (Oxford GlycoSystems Ltd.). This instrument is an integrated chromatography instrument designed to fractionate mixtures of uncharged glycans. If the labelled pool of glycans contains acidic substituents, these should be removed by appropriate enzymatic or chemical means.

EXAMPLE 2

To follow the conjugation of 2AB to glycans under different reaction conditions, two model N-glycans were used as substrates, namely the asialo biantennary N-glycan (NA2) and the asialo biantennary N-glycan with core fucose (NA2F). The 2AB-conjugated form of each glycan elutes at a different position from the un-conjugated form during gel permeation chromatography using the GlycoMap 1000 (Oxford GlycoSystems Ltd.). The following assay procedure was therefore used to investigate the extent of conjugation under different reaction conditions.

Radio-labelled ($^3$H at C-6 of galactose) unreduced NA2 and NA2F were prepared by galactosylation of the corresponding asialo agalacto biantennary glycans (using β-galactosyl transferase and UDP-($^3$H) galactose), and purified using the GlycoMap 1000. Trace amounts of radio-labelled glycans were mixed with known amounts of the corresponding un-labelled glycan, conjugated with 2AB under chosen conditions, and the products separated (after removal of unreacted 2AB and salts by paper chromatography) using the GlycoMap 1000. The relative amount of radioactivity in the conjugated and unconjugated glycans is a direct measure of the relative mole per cent conjugation of the glycan to 2AB, and was found to be 85%.

EXAMPLE 3

Microgram quantities of hydrolysed dextran, the oligosaccharides NA2, NA2B and the oligosaccharide libraries released from bovine fetuin, human α1-acid glycoprotein, bovine pancreas ribonuclease B and chicken ovalbumin, were dried in polypropylene microcentrifuge tubes. 5 µl of a solution containing 1M sodium cyanoborohydride and 350 mM 2-aminobenzoic acid (anthranilic acid, 2AA) in 30% acetic acid/dimethyl sulfoxide, was added. The samples were incubated at 65° C. for 2 hours and then dried again before being re-dissolved in sample buffer consisting of 125 mM Tris HCl pH 6.8, 0.01% bromophenol blue and 20% glycerol. 4 µl of each sample was then loaded onto a polyacrylamide mini-gel (75×85×0.75 mm) consisting of a stacking gel composed of 10% acrylamide, 3% bisacrylamide and 125 mM Tris/HCl buffer pH 6.8, and a resolving gel composed of 25% acrylamide, 5% bisacrylamide and 375 mM Tris/HCl pH 8.8. The samples were run on the gel using a reservoir buffer composed of 40 mM Tris/borate pH 8.8, at constant current of 16 mA for 90 minutes. The gel was removed from the apparatus and visualised using a UV transilluminator with emission maximum 312 nm. The gel could be examined and/or photographed either before or after drying in conventional gel drying apparatus.

A photograph (taken as described) of a dry gel showed

| | |
|---|---|
| lane 1 | hydrolysed dextran |
| lane 2 | ovalbumin |

-continued

| lane 3 | ribonuclease B |
| lane 4 | bovine fetuin |
| lane 5 | NA2 |
| lane 6 | NA2B |
| lane 7 | α1-acid glycoprotein |
| lane 8 | hydrolysed dextran |

Chart A oligo-CHO +

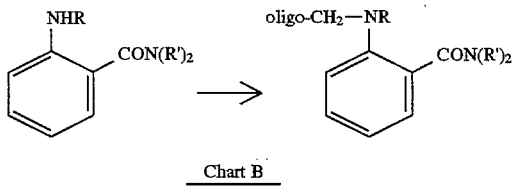

Chart B oligo-CH$_2$-NHR' +

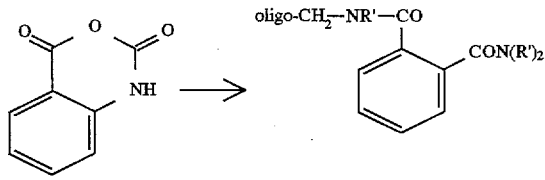

We claim:

1. A method for distinguishing between carbohydrates or glycoconjugates in a mixture thereof comprising labelling each carbohydrate or glycoconjugate in the mixture at the reducing terminal with a —NR—Ph—CO— group to produce hydrophilic fluorescently labelled saccharide molecules having a formula selected from the group consisting of oligo—CH$_2$—NR—Ph—CON(R')$_2$ and oligo—CH$_2$—NR'—CO—Ph—NHR, and separating the fluorescently labelled saccharide molecules through detection of the fluorescent label, wherein R and R' are independently selected from the group of H and C$_1$ to C$_6$ alkyl and Ph is phenylene.

2. A method according to claim 1, wherein R is H.

3. A method according to claim 1, wherein Ph is o-phenylene.

4. A method according to claim 1, wherein the separating is done by gel electrophoresis.

5. A method according to claim 1, wherein the separating is done by chromatography.

6. A method according to claim 1, wherein R' is H.

7. A labelled saccharide having the formula oligo—CH$_2$—NR—Ph—CON(R')$_2$ obtainable from an oligo saccharide represented as oligo-CHO, wherein R and R' are independently selected from the group of H and C$_1$ to C$_6$ alkyl and Ph is phenylene.

8. A saccharide according to claim 7, wherein R' is H.

9. A saccharide according to claim 7, wherein R is H.

10. A saccharide according to claim 7, wherein Ph is o-phenylene.

11. A labelled saccharide having the formula oligo—CH$_2$—NR'—CO—Ph—NHR obtainable from an oligo saccharide represented as oligo—CHO, wherein R and R' are independently selected from the group of H and C$_1$ to C$_6$ alkyl and Ph is phenylene.

12. A saccharide according to claim 11, wherein the or each R' is H.

13. A saccharide according to claim 11, wherein R is H.

14. A saccharide according to claim 11, wherein Ph is o-phenylene.

* * * * *